(12) United States Patent
Prinzhausen et al.

(10) Patent No.: US 6,934,027 B2
(45) Date of Patent: Aug. 23, 2005

(54) INTERFEROMETRIC MEASURING DEVICE

(75) Inventors: Friedrich Prinzhausen, Stuttgart (DE);
Michael Lindner, Leutenbach (DE);
Vincent Thominet, Echandens (CH)

(73) Assignee: Robert Bosch GmbH, Stuttgart (DE)

( * ) Notice: Subject to any disclaimer, the term of this patent is extended or adjusted under 35 U.S.C. 154(b) by 504 days.

(21) Appl. No.: 10/070,572

(22) PCT Filed: Jul. 6, 2001

(86) PCT No.: PCT/DE01/02517

§ 371 (c)(1),
(2), (4) Date: Jul. 10, 2002

(87) PCT Pub. No.: WO02/04888

PCT Pub. Date: Jan. 17, 2002

(65) Prior Publication Data

US 2002/0180982 A1 Dec. 5, 2002

(30) Foreign Application Priority Data

Jul. 7, 2000 (DE) ........................................ 100 33 028
Jul. 3, 2001 (DE) ........................................ 101 31 779

(51) Int. Cl.[7] ........................... G01N 21/25; G01B 9/02; G01B 11/02
(52) U.S. Cl. ....................... 356/417; 356/479; 356/489; 356/495; 356/497; 356/516
(58) Field of Search ................................. 356/417, 479, 356/489, 495, 496, 497, 498, 516, 509, 510

(56) References Cited

U.S. PATENT DOCUMENTS 5,369,489 A * 11/1994 Somekh
5,392,116 A * 2/1995 Makosch
5,398,113 A * 3/1995 de Groot
5,426,504 A * 6/1995 Callender
5,933,237 A * 8/1999 Drabarek
6,002,480 A * 12/1999 Izatt et al.
6,038,027 A * 3/2000 Marcus et al.
6,195,168 B1 * 2/2001 De Lega et al.

FOREIGN PATENT DOCUMENTS

| DE | 41 08 944 | 9/1992 |
|----|-----------|--------|
| DE | 197 21 843 | 2/1999 |
| DE | 198 08 273 | 9/1999 |
| EP | 0 534 795 | 3/1993 |

OTHER PUBLICATIONS

J. Mod. Opt., vol. 42, No. 2, 389–401, 1995.
Th. Dresel, G. Häusler, H. Venzke, "Three–dimensional sensing of rough surfaces by coherence radar," Appl. Opt., vol. 31 No. 7, 919–925, 1992.

* cited by examiner

Primary Examiner—Frank G. Font
Assistant Examiner—Khaled Brown
(74) Attorney, Agent, or Firm—Kenyon & Kenyon

(57) ABSTRACT

An interferometric measuring device for measuring the shape of a surface of an object having a radiation source which emits a short-coherent radiation, a beam splitter for forming an object beam which is directed via an object light path to the object, and a reference beam which is directed via a reference light path to a reflective reference plane, and having an image converter which picks up the radiation reflected back by the surface and the reference plane and brought to interference, and sends it to an analyzing device for determining a measuring result pertaining to the surface, the optical length of the object light path being changed relative to the optical length of the reference light path for analyzing the interference peak.

24 Claims, 5 Drawing Sheets

INTERFEROMETRIC MEASURING DEVICE

FIELD OF THE INVENTION

The present invention relates to an interferometric measuring device for measuring the shape of the surface of an object, using a radiation source emitting short-coherent radiation. The present invention includes a beam splitter for forming an object beam directed to the object via an object light path and for forming a reference beam directed to a reflecting reference plane via a reference light path. The device also includes an image converter which picks up the radiation reflected from the surface and the reference plane and brought to interference, and sends it to an analyzing device for determining a measuring result pertaining to the surface, the optical length of the object light path being altered relative to the optical length of the reference light path.

BACKGROUND INFORMATION

An interferometric measuring device of this type is described in German Published Patent Application No. 41 08 944 (where the scanning of an intermediate image given as an alternative in the present document is not mentioned). With this interferometric measuring device based on the measuring principle of white-light interferometry or short-coherence interferometry, a radiation source emits short-coherent radiation which is split by a beam splitter into an object beam which illuminates a measuring object and a reference beam which illuminates a reflective reference plane in the form of a reference mirror. To scan the object surface in the depth direction, the reference mirror is moved in the direction of the optical axis of the reference light path by a piezo control element. When the object light path corresponds to the reference light path, the maximum interference contrast is obtained in the area of the coherence length and is detected by a photoelectric image converter and a downstream analyzing device and is analyzed on the basis of the known deflection position of the reference mirror to determine the contour of the object surface.

Additional interferometric measuring devices and interferometric measuring methods based on white-light interferometry are described by P. de Groot, L. Deck, "Surface profiling by analysis of white-light interferograms in the spatial frequency domain" J. Mod. Opt., Vol. 42, No. 2,389–401, 1995 and Th. Dresel, G. Häusler, H. Venzke, "Three-dimensional sensing of rough surfaces by coherence radar," Appl. Opt., Vol 31 no. 7,919–925, 1992.

In German Patent Application No. 199 48 813 (not pre-published) such an interferometric measuring device based on white light interferometry is also shown, the lateral resolution being increased particularly for measurement in narrow cavities by creating an intermediate image in the objective light path. German Patent Application No. 100 15 878.1, likewise not published previously, proposes scanning of an intermediate image to increase the depth of focus, with a relatively high lateral resolution at the same time.

There are problems with the current interferometric measuring devices and measuring methods if the measurement task requires scanning of several separated surfaces which are several millimeters apart, for example, and/or are oriented at an inclination to one another.

SUMMARY OF THE INVENTION

An object of the present invention is to provide an interferometric measuring device with which at least two spatially separated surfaces may be measured with accurate and highly reproducible measurement results.

This object is achieved by the present invention. According to the features of the present invention, superposition optics having multifocal optics or free segment optics are provided from various imaging elements in the object light path.

Simultaneously, using the superposition optics, an image may be created of at least one further surface in addition to the surface, which are imaged directly, or via at least one intermediate image in the object light path, on the image converter. The measurement of the surface and of the at least one further surface occurs accompanied by a relative change in the optical length of the object light path to the optical length of the reference light path (scan). Alternatively, in the object light path, imaging optics having a depth of focus of at least the optical path difference of the two surfaces is provided, which may be used to simultaneously produce an image, apart from that of the surface, of at least one further surface disposed in front of it or behind it and parallel to it, or of surfaces arranged at an angle or at right angles to one another via optical deflection elements, and this image is imaged via at least one intermediate image in the object light path on the image converter, and that the measurement of the surface and of the at least one further surface takes place accompanied by a relative change in the optical length of the object light path to the optical length of the reference light path.

Using these techniques, exact measurement of the different surfaces is made possible, without renewed alignment of the object light path. For registering the reference maximum, the optical lengths of the reference light path and of the object light path are set one after the other in correspondence to the positions of the various surfaces. In this connection, the free-segment optics may be easily adapted, for example, even to surfaces placed at an angle to each another or surfaces lying opposite each other. Using the multifocal optics, and also using imaging optics having a depth of focus of at least the optical path difference of the two surfaces, surfaces may be measured which are far removed from each other and oriented differently to each other, and also, for example, their parallelism or surface evenness, thickness and diameter.

Various other example embodiments also include the feature that the object light path for generating a common intermediate image of the surface and of the intermediate image of the additional surface(s) is formed in a common intermediate image plane in the object light path, and that the common intermediate image is imaged on the image converter either directly or by way of at least one intermediate image. With at least one intermediate image, scanning an intermediate image is possible. Additionally an increased lateral resolution may be obtained.

A measurement having lateral resolution, even in narrow cavities, may be achieved provided that the object light path is formed as an endoscope.

To achieve accurate measurement results, an optical fiber is provided for illuminating the object with a planar wave, the fiber output on the object end may be situated in a telecentric imaging arrangement of the object light path, or that an illumination light path having additional lenses and deflector elements is formed.

The measurement is made possible or further facilitated when the reference light path has optics similar or identical to that of the object light path, making it possible to produce the interference or optimize the interference contrast or compensate for optical effects of the components in the object light path.

Options for easily measuring various surfaces, even in hard-to-reach places, are obtained when an optical system, that is rigid relative to the object, is situated in the object light path, and that the rigid optical system is followed by an optical system that is movable in the direction of its optical axis.

A favorable design for the construction and handling is to have the rigid optics be a part of the superposition optics.

To achieve a measurement with respect to relative lateral movement of the object, the rigid optics may produce images toward infinity.

Furthermore, the rigid optics may be designed as superposition optics, which are used to produce at least one intermediate image that is rigid relative to the object, and an objective optical system, designed as movable optics following behind the rigid intermediate image in the path of the beam, movable in the direction of its optical axis for scanning the intermediate image which is normally aligned to this axis in the depth direction and is designed for imaging the same directly on the image converter or by way of one or more intermediate images. Due to the creation of the rigid intermediate image of the object surface situated, for example, in the object light path using the superposition optics in the object light path, the object surface to be measured is detectable with a relatively high lateral resolution, even in narrow channels or boreholes, and is evaluable with regard to the depth structure by using the image converter or the downstream analyzing device. The rigid intermediate image is scannable with relatively simple measures because only few optical components of the object light path need be moved for the depth scanning, the scanned depth of the rigid intermediate image, in each case, remains within the range of the depth of focus of the movable objective optics due to the depth scanning (depth scan). The object plane of the moving objective optics is moved through the rigid intermediate image, such that, for example, the interference peaks are analyzed in the area of the greatest depth of focus.

The imaging quality and the accuracy of the analysis are such that the intermediate image has the same linear magnification for all object points imaged in the intermediate image. The design may be configured to allow the rigid optics to be formed as a $4f$ arrangement.

With respect to the design of the rigid optics and the movable optics, German Patent Application No. 101 15 524 by the same applicant provides additional information.

DETAILED DESCRIPTION

Figure 1:
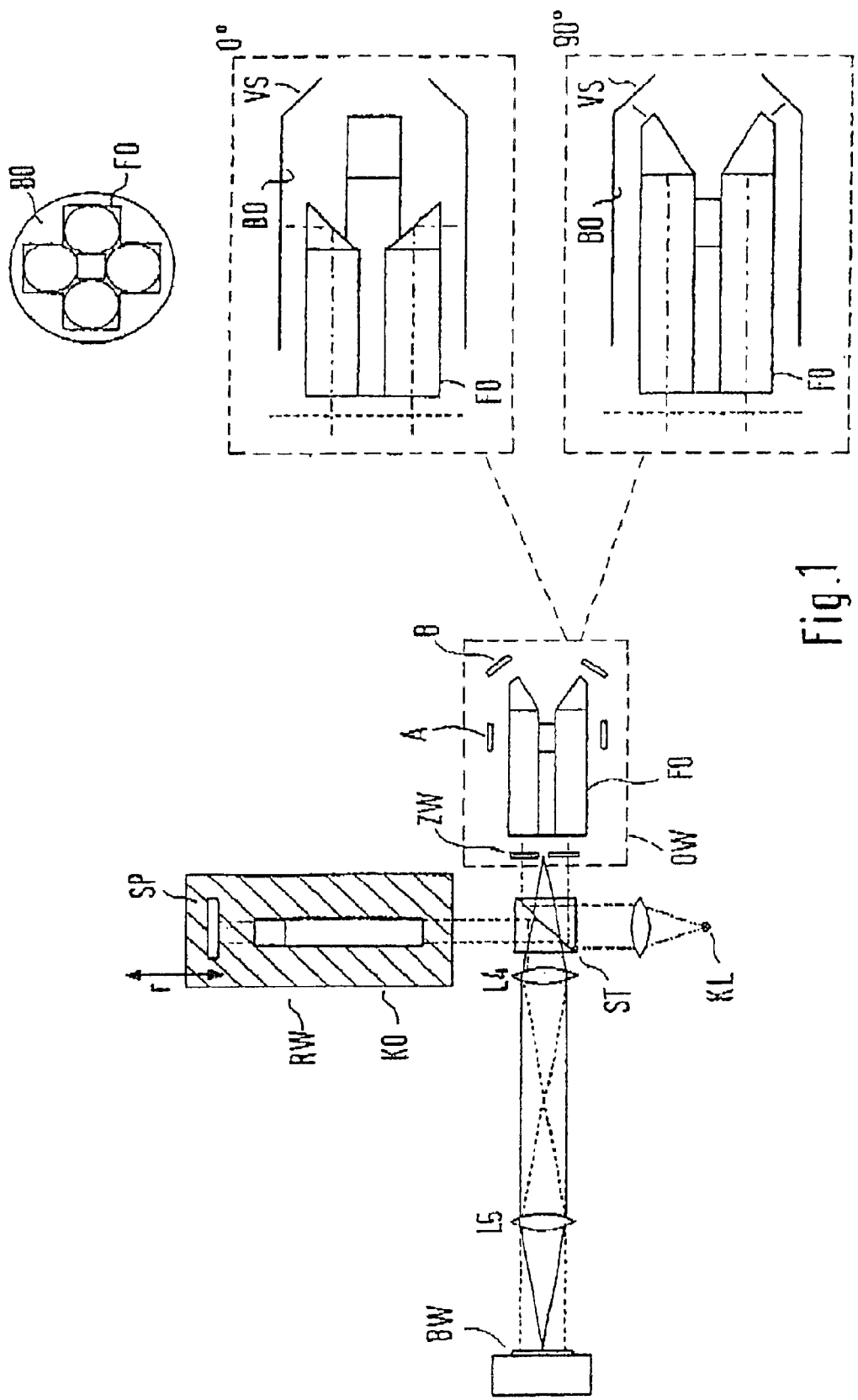
FIG. 1 is a schematic diagram of an interferometric measuring device according to the principle of white-light interferometry (short-coherence interferometry) having a free-segment optical system, the free-segment optical system being illustrated in two positions rotated by 90° relative to each other.

Referring to FIG. 1, an interferometric measuring device based on the principle of white-light interferometry (short-coherence interferometry) has an object light path OW, a reference light path RW, an image converter BW having a downstream analyzing device. Interference occurs only in the area of the coherence length, permitting simple coordination of the optical path lengths of reference light path RW and object light path OW as well as, for example, detection of the interference peak. Radiation emitted by a short-coherent light source KL has a coherence length on an order of magnitude such as 10 $\mu$m. The radiation of short-coherent light source KL is split by a beam splitter ST into a reference beam, which is guided via reference light path RW, and an object beam, which is guided via object light path OW. A fourth and fifth lens L4, L5 are situated in the light path to image converter BW for imaging.

The measurement is made possible or further facilitated such that the reference light path has optics similar or identical to that of the object light path, making it possible to produce the interferences or optimize the interference contrast or compensate for optical effects of the components in the object light path.

As a further feature, a superposition optics arrangement in the form of a free-segment optics FO is arranged in object light path OW, and is represented in the diagrams on the right-hand side in cross section (upper diagram), in a 0° view (middle diagram) and in a 90° view (lower diagram) in a state in which a valve boring BO is carried up to the vicinity of a valve seat VS. As an additional feature, superposition optics in the form of a free-segment optics FO is situated in object light path OW and shown in cross section (top diagram) in a 0° view in the illustration shown at the right (middle diagram) and in a 90° view (bottom diagram) in a state in which it is guided into a valve bore BO in proximity to a valve seat VS. Several separate surfaces A, B of bore BO or of valve seat VS may be detected at the same time with free-segment optics FO and imaged in a common intermediate image ZW in an intermediate image plane in the object light path, which is perpendicular to a main optical axis of object light path OW. Free-segment optics FO has several light deflecting surfaces and imaging refracting elements and is adapted to the respective measurement requirements. In particular, surfaces A, B situated at different distances from common intermediate image ZW and also situated at an inclination to each other or opposite to each other may be detected and imaged in the common intermediate image ZW.

Detecting the interference maxima corresponding to the two surfaces A, B occurs by changing reference light path RW corresponding to a scanning direction r. The moved unit is shown by dotted lines.

Superposition optics situated in object light path OW has two collimated lenses, namely a first tens L1 and a second lens L2 having different focal lengths, which may have prism-shaped elements situated in front of them. The object light path is also designed for producing a telecentric image. Surfaces A, B situated parallel to one another and different distances apart, e.g., a few $\mu$m to more than 1 cm, and perpendicular to the main optical axis of object light path OW, are imaged in an intermediate image plane in the object light path with two lenses L1 and L2 in common intermediate image ZW composed of intermediate image ZA of surface A and intermediate image ZB of surface B. The focal lengths of first and second lenses L1, L2 are given as $F_A$, $F_B$. In addition, a third lens L3 for imaging is situated in the beam path of object light path OW. To record the interference peak, mirror SP is moved in the scanning direction r.

Figure 2:
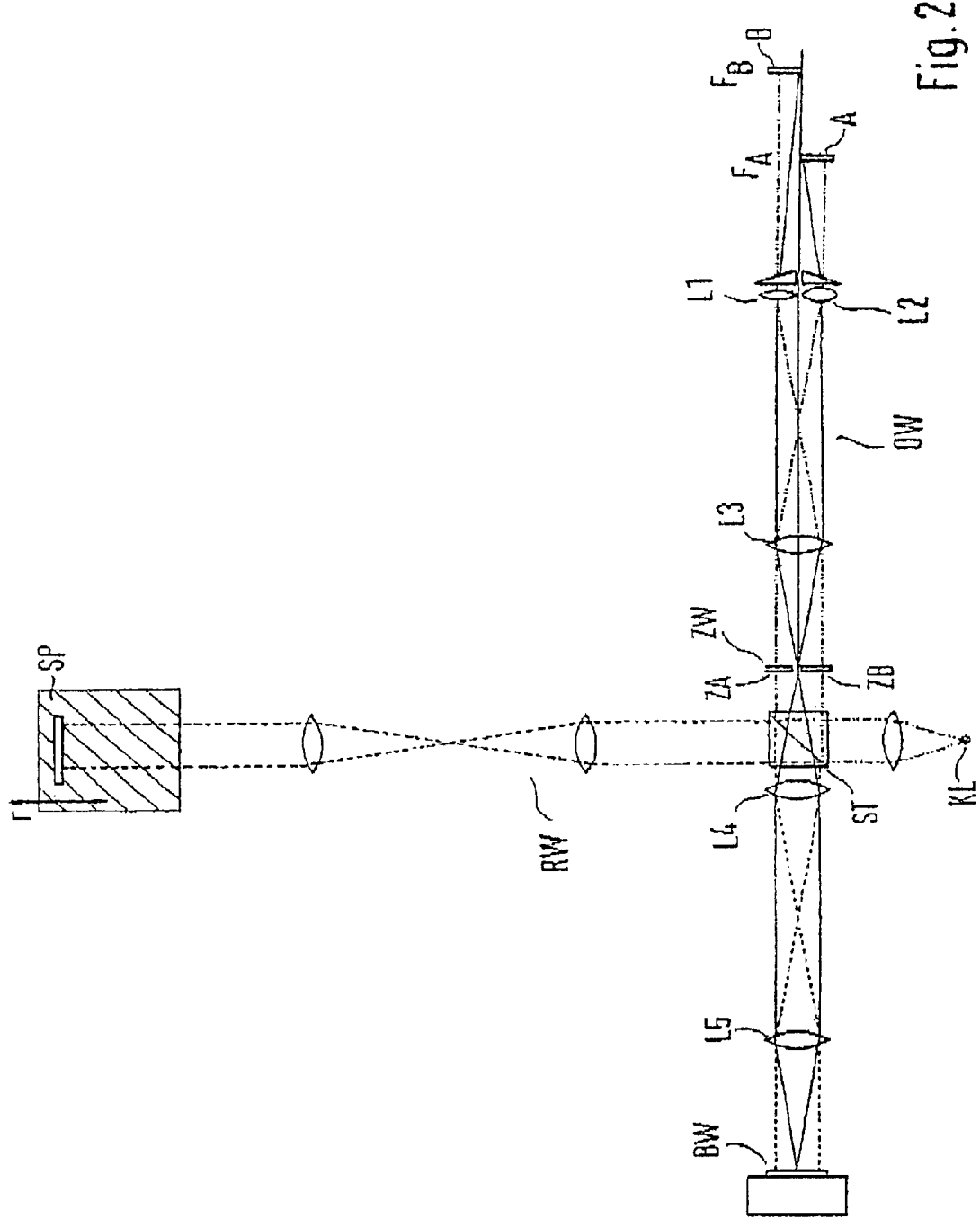
FIG. 2 is a further example embodiment of the interferometric measuring device, superposition optics having separated refracting elements in the object light path.
Figure 3:
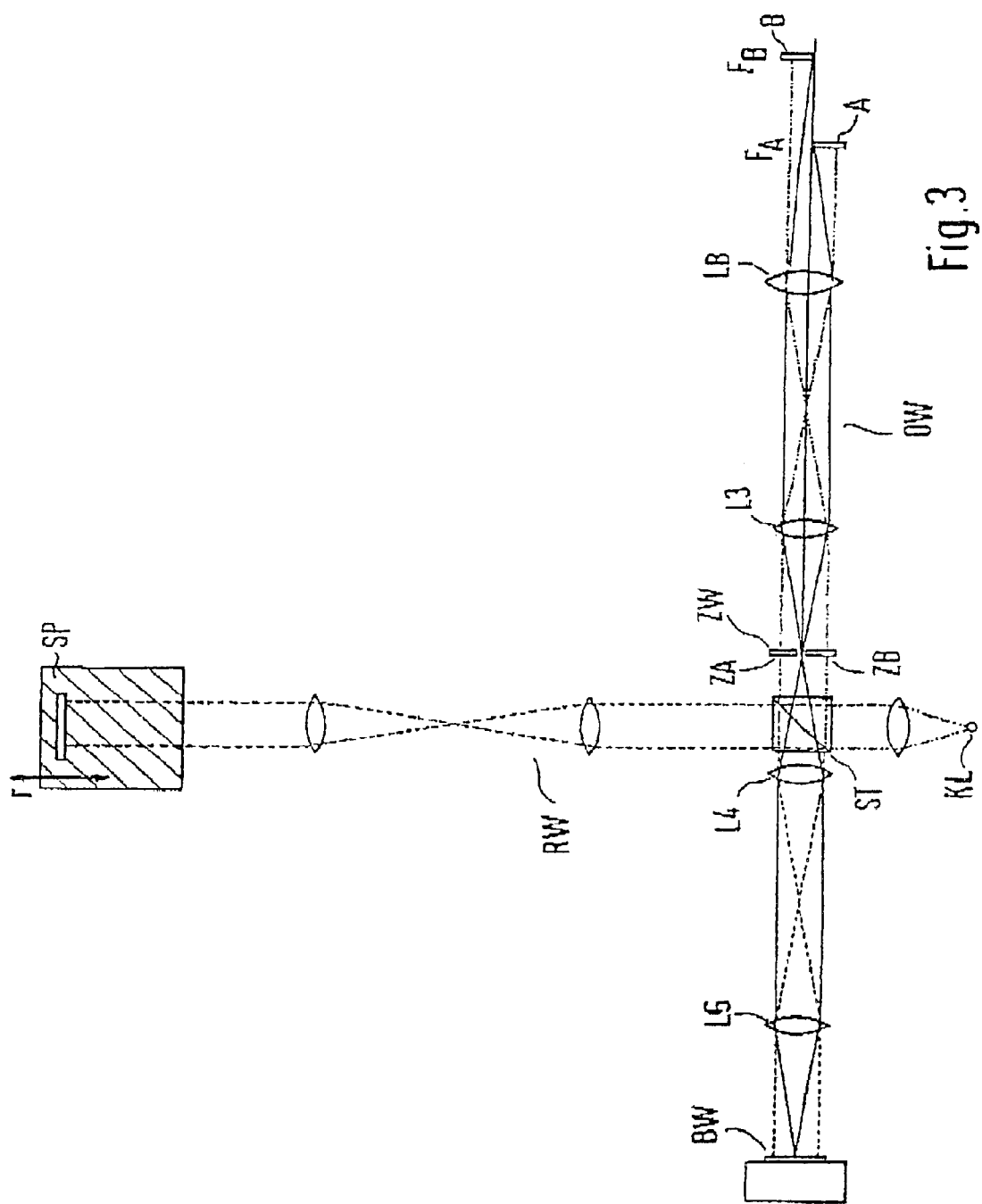
FIG. 3 is another example embodiment of an interferometric measuring device, wherein bifocal optics are situated in the object light path.

FIG. 3 illustrates an example embodiment of the interferometric measuring device in which, as opposed to FIG. 2, instead of two lenses L1, L2, a bifocal optics LB is situated, the optics properties corresponding approximately to those of the two lenses L1, L2.

Figure 4:
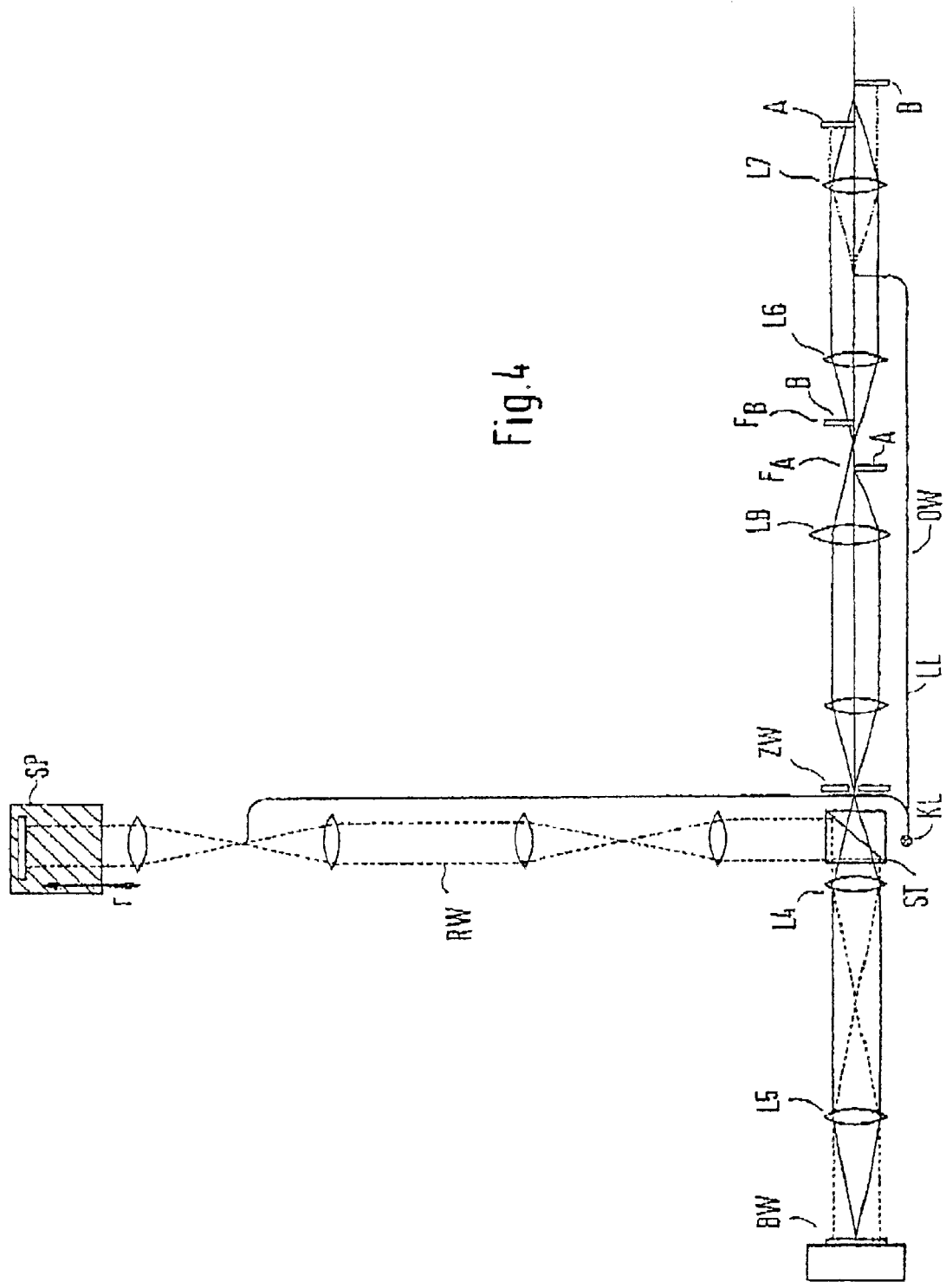
FIG. 4 is another example embodiment of an interferometric measuring device in which the radiation in the reference light path and in the object light path is guided by optical fibers.

In the example embodiment illustrated in FIG. 4, additional lenses L6, L7 are introduced into the beam path of the object light path of bifocal optics LB on the object side. In addition, an optical fiber LL via which short-coherent radiation is conveyed from radiation source KL to illuminate surfaces A, B with a planar wave front via additional lens L7 is also situated in object light path OW. Corresponding lenses are also situated in reference light path RW for compensation and the radiation is also passed in the object light path via an optical fiber.

Figure 5:
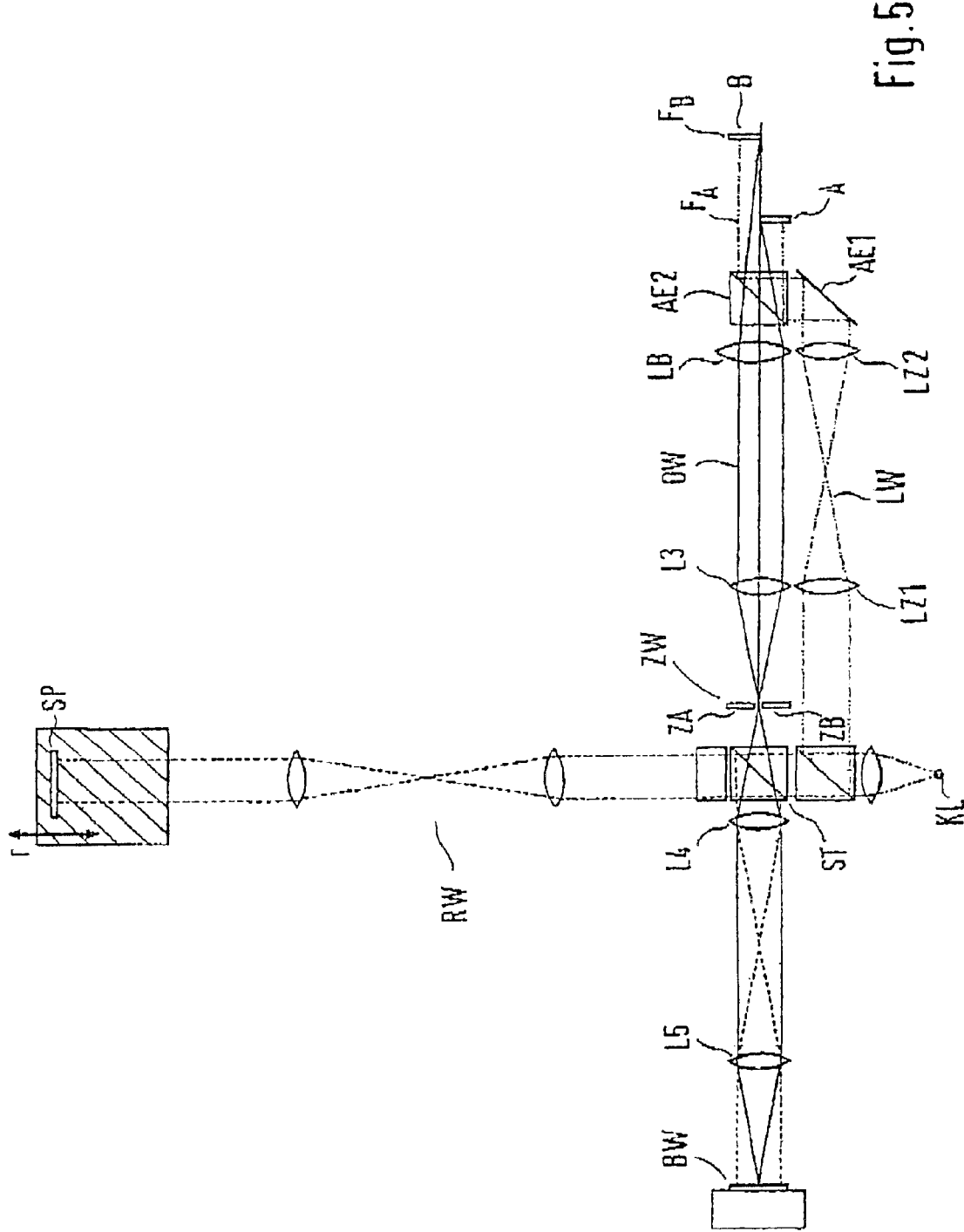
FIG. 5 is another example embodiment of the interferometric measuring device in which the radiation is guided in the object light path via an illumination light path having lenses and deflector elements.

In FIG. 5, in comparison with FIG. 4, optical fiber LL in object light path OW is replaced by an imaging light path LW having discrete additional lenses LZ1, LZ2 and deflector elements AE1, AE2 to illuminate surfaces A, B with a planar wave. Additional lenses L6, L7 are not provided.

Surfaces A, B that are spatially separated from one another may be measured at the same time using the interferometric measuring devices described above and special optics in the form of the superposition optics mentioned above. The distance apart, and/or thickness, parallelism and diameter of spatially separated surfaces A, B may be measured in this way. The spatially separated surfaces may be imaged on image converter BW directly or via a common intermediate image ZW in the object light path.

Common intermediate image ZW may be imaged, directly or by way of one or more intermediate images in the object light path, on image converter BW, e.g., a CCD camera.

The design of the interferometric measuring device is implemented in the form of a Michelson interferometer, for example. Short coherent radiation source KL may be, for example, a superluminescence diode or an LED. With illumination through the superposition optics, spatially separated surfaces A, B of the object are illuminated, in separate surfaces A, B are illuminated with almost planar waves.

The superposition optics in the form of free-segment optics FO may be composed, for example, of various individual lens systems which image different surfaces along different optical axes and with different optical path lengths in the common intermediate image plane. Free-segment optics FO may be implemented in the form of optical elements such as spherical lenses, aspherical lenses, rod lenses or Grin lenses or diffractive optical elements or prisms or mirrors, which may also be combined with one another.

Instead of the design of superposition optics as a bifocal optics LB, multifocal optics may also be used if more surfaces are to be measured. The multifocal optics may be combined with another lens to form a telecentric arrangement, for example.

For compensation of the optical path lengths and the dispersion in both arms of the interferometer, namely reference light path RW and object light path OW, the fiber lengths and geometries of the optical fibers used may be as identical as possible.

The superposition optics may also be implemented approximately by optics having a great depth of focus or with an expanded depth of focus such as Axicon.

In the case of multifocal optics or bifocal optics as the superposition optics, optics having only one focal plane may also be used for compensation in reference light path RW, as shown in FIG. 3.

An image of surfaces A, B to be observed superimposed by the reference wave is produced on image converter BW. For data analysis, a change is produced in the path difference between the optical path lengths in the object light path and the reference light path (deep scan), the change caused by scanning movement r, for example. Various procedures may be provided to change the difference in path, e.g., movement of the reference mirror, movement of the object in the depth direction, movement of the objective in the depth direction, movement of the entire sensor relative to the object or intermediate image scanning according to German Patent Application No. 100 15 878 or a change in the optical path length due to acousto-optical modulators.

An interference contrast occurs in the image of the object when the path difference in both interferometer arms is less than the coherence length. For obtaining the 3-D height profile, various methods are established. During depth scanning, the path difference is detected, for each image point (pixel), at which the highest fringe contrast occurs.

What is claimed is:

1. An interferometric measuring device for measuring a shape of a surface of an object, comprising:

a radiation source that emits a short-coherent radiation;

a beam splitter for forming an object beam which is directed via an object light path to the object, and a reference beam which is directed via a reference light path to a reflective reference plane;

an image converter for detecting a radiation reflected back by the surface and the reference plane and brought to interference, and for transmitting the radiation;

an analyzing device for receiving the radiation transmitted from the image converter and for determining a measuring result pertaining to the surface, wherein an optical length of the object light path is altered relative to an optical length of the reference light path to perform a measurement; and a superposition optics positioned in the object light path and including one of multifocal optics and a free segment optics having imaging elements, the superposition optics creating an image simultaneously other than of the surface, of at least one additional surface, the image of the at least one additional surface and the image of the surface being imaged on the image converter one of directly and via at least one intermediate image in the object light path, wherein a measurement of the surface and a measurement of the at least one additional surface occurs accompanied by a relative change in the optical length of the object light path as compared to the optical length of the reference light path.

2. The interferometric measuring device according to claim 1, wherein the free segment optics accommodates the surface and the at least one additional surface orientated at an angle to each other.

3. The interferometric measuring device according to claim 1, wherein the object light path generates a common intermediate image of the surface and an intermediate image of the at least one additional surface in a common intermediate image plane in the object light path, and the common intermediate image is imaged one of directly on the image converter and via the at least one intermediate image.

4. The interferometric measuring device according to claim 3, wherein a scanning of the common intermediate image is performed.

5. The interferometric measuring device according to claim 1, further comprising:
an endoscope serving as the object light path.

6. The interferometric measuring device according to claim 1, further comprising one of:
an optical fiber for illuminating the object with a planar wave and including an output situated at an object end in a telectric image arrangement of the object light path; and
an illumination light path formed with additional lenses and deflector elements.

7. The interferometric measuring device according to claim 1, further comprising:
optics positioned in the reference light path similar to those of the object light path.

8. The interferometric measuring device according to claim 1, further comprising:
optics positioned in the reference light path identical to those of the object light path.

9. The interferometric measuring device according to claim 1, further comprising:
an optics rigid with respect to the object positioned in the object light path; and
an optics following the rigid optics and being movable in a direction of an optical axis thereof.

10. The interferometric measuring device according to claim 9, wherein the rigid optics are part of the superposition optics.

11. The interferometric measuring device according to claim 10, wherein the rigid optics image toward infinity.

12. An interferometric measuring device for measuring a shape of a surface of an object, comprising:
a radiation source that emits a short-coherent radiation;
a beam splitter for forming an object beam which is directed via an object light path to the object, and a reference beam which is directed via a reference light path to a reflective reference plane;
an image converter for detecting a radiation reflected back by the surface and the reference plane and brought to interference, and for transmitting the radiation;
an analyzing device for receiving the radiation transmitted from the image converter and for determining a measuring result pertaining to the surface wherein an optical length of the object light path is altered relative to an optical length of the reference light path to perform a measurement; and
an imaging optics arranged in the object light path and for providing a depth of focus of at least an optical path difference of the surface and another surface, the imaging optics simultaneously creating an image other than that of the surface, of at least one further parallel surface arranged one of in front of, behind, configured at an angle and at right angles via optical deflecting elements, the image of the at least one further parallel surface being imaged on the image converter via at least one intermediate image in the object light path, a measurement of the surface and of the at least one further parallel surface occurring through a relative change in the optical length of the object light path, as compared to the optical length of the reference light path.

13. The interferometric measuring device according to claim 12, wherein the object light path generates a common intermediate image of the surface and an intermediate image of the at least one additional surface in a common intermediate image plane in the object light path, and the common intermediate image is imaged one of directly on the image converter and via the at least one intermediate image.

14. The interferometric measuring device according to claim 12, wherein a scanning of the common intermediate image is performed.

15. The interferometric measuring device according to claim 12, further comprising:
an endoscope serving as the object light path.

16. The interferometric measuring device according to claim 12, further comprising one of:
an optical fiber for illuminating the object with a planar wave and including an output situated at an object and in a telectric image arrangement of the object light path; and
an illumination light path formed with additional lenses and deflector elements.

17. The interferometric measuring device according to claim 12, further comprising:
optics positioned in the reference light path similar to those of the object light path.

18. The interferometric measuring device according to claim 12, further comprising:
optics positioned in the reference light path identical to those of the object light path.

19. The interferometric measuring device according to claim 12, further comprising:
an optics rigid with respect to the object positioned in the object light path to form a rigid optics; and
an optics following the rigid optics and being movable in a direction of an optical axis thereof.

20. The interferometric measuring device according to claim 19, wherein the rigid optics are part of a superposition optics.

21. The interferometric measuring device according to claim 20, wherein the rigid optics image toward infinity.

22. The interferometric measuring device according to claim 19, wherein the rigid optics, is configured as a superposition optics to produce one intermediate image rigid with respect to the object, and
an objective optics arranged as a movable optics positioned to follow in the optical path behind the rigid intermediate image and formed on the image converter movable in a direction of an optical axis of the image converter in a depth direction and the objective optics further arranged to at least one of direct image scan and scan via at least one intermediate image.

23. The interferometric measuring device according to claim 19, wherein the rigid optics are arranged as a 4f configuration.

24. The interferometric measuring device according to claim 12, wherein the at least one intermediate image has the same linear magnification for all object points imaged in the at least one intermediate image.

* * * * *